(12) United States Patent
Bergmann

(10) Patent No.: US 7,517,518 B2
(45) Date of Patent: Apr. 14, 2009

(54) METHOD FOR DIAGNOSIS OF SEPSIS WITH DETERMINATION OF CA 125

(75) Inventor: Andreas Bergmann, Berlin (DE)

(73) Assignee: B.R.A.H.M.S Aktiengesellschaft, Hennigsdorf (DE)

( * ) Notice: Subject to any disclaimer, the term of this patent is extended or adjusted under 35 U.S.C. 154(b) by 0 days.

(21) Appl. No.: 10/496,173

(22) PCT Filed: Nov. 27, 2002

(86) PCT No.: PCT/EP02/13391

§ 371 (c)(1),
(2), (4) Date: Nov. 5, 2004

(87) PCT Pub. No.: WO03/048776

PCT Pub. Date: Jun. 12, 2003

(65) Prior Publication Data

US 2005/0074811 A1 Apr. 7, 2005

(30) Foreign Application Priority Data

Dec. 4, 2001 (EP) .................................. 01128848

(51) Int. Cl.
*A61K 49/00* (2006.01)
*A61K 39/38* (2006.01)
*A01N 63/00* (2006.01)
*G01N 33/554* (2006.01)
*G01N 33/53* (2006.01)

(52) U.S. Cl. ..................... 424/9.1; 424/93.4; 424/184.1; 435/7.32; 435/7.31

(58) Field of Classification Search ................... 435/7.1, 435/7.31, 7.32; 424/9.1, 93.4, 184.1
See application file for complete search history.

(56) References Cited

U.S. PATENT DOCUMENTS

| | | | | | |
|---|---|---|---|---|---|
| 5,366,866 | A | * | 11/1994 | Xu et al. ..................... | 435/7.23 |
| 5,536,382 | A | * | 7/1996 | Sunzeri ....................... | 204/451 |
| 5,639,617 | A | * | 6/1997 | Bohuon ....................... | 435/7.1 |
| 5,660,994 | A | | 8/1997 | Bruder-Heid et al. ...... | 435/7.23 |
| 7,132,246 | B2 | | 11/2006 | Bergmann et al. | |
| 7,157,081 | B2 | | 1/2007 | Bergmann et al. | |
| 2004/0010121 | A1 | * | 1/2004 | Birse et al. .................. | 530/350 |
| 2004/0253637 | A1 | * | 12/2004 | Buechler et al. ............ | 435/7.1 |
| 2005/0059104 | A1 | * | 3/2005 | Bergmann ................. | 435/7.32 |
| 2005/0064506 | A1 | * | 3/2005 | Bergmann .................. | 435/7.1 |
| 2005/0106645 | A1 | * | 5/2005 | Bergmann ................. | 435/7.32 |
| 2005/0239150 | A1 | | 10/2005 | Bergmann et al. | |
| 2006/0029990 | A1 | | 2/2006 | Bergmann et al. | |
| 2006/0035221 | A1 | | 2/2006 | Bergmann et al. | |
| 2006/0115869 | A1 | | 6/2006 | Bergmann et al. | |
| 2006/0234295 | A1 | | 10/2006 | Bergmann et al. | |

FOREIGN PATENT DOCUMENTS

WO     WO 91/04927     * 3/1994

OTHER PUBLICATIONS

Moore et al (Clinical Utility of CA 125 Levels in Predicting Laparoscopically Confirmed Salpingitis in Patients With Clinically Diagnosed Pelvic Inflammatory Disease, Infectious Disease in Obstetrics and Gynecology, 1998; 6: 182-185).*
Petaja, J. et al (Serum Tumor Marker CA 125 Is an Early and Sensitive Indicator of Veno-Occulusive Disease in Children Undergoing Bone Marrow Transplantation, Clinical Cancer Research, 2000; 6: 531-535).*
Camera, A. et al (Increased CA 125 Serum Levels in Patients with Advance Acute Leukemia with Serosal Involvement, Cancer, 2000; 88: 75-8).*
Medline Plus Medical Encyclopedia: Sepsis (http:www.nlm.nih.gov/medlineplus/ency/article/000666.htm, pp. 1-3).*
Petaja, J. et al. (Clinical Cancer Research, 2000; 6: 531-535).*
Medline Plus Medical Encyclopedia: Sepsis (http://nlm.nih.gov/medlineplus/ency/article/000666.htm, pp. 1-3).*
Aird, "The Hematologic System as a Marker of Organ Dysfunction in Sepsis," *Mayo Clin, Proc.*, 78:869-881, 2003.
Assicot, et al., "High Serum Procalcitonin Concentrations in Patients with Sepsis and Infection, " *Lancet*, 341(8844):515-518, 1993.

(Continued)

*Primary Examiner*—Mark Navarro
*Assistant Examiner*—Lakia J Tongue
(74) *Attorney, Agent, or Firm*—Heslin Rothenberg Farley & Mesiti P.C.

(57) ABSTRACT

The invention relates to a method for the early differential diagnosis and detection, prognosis and determination of the degree of severity of a case of sepsis and systemic infections similar to sepsis and also for the determination of the course of infection during therapy. The above is achieved, whereby the amount of CA 125 in a biological fluid from a patient is determined, preferably with determination of at least one further parameter suitable for diagnosis of sepsis, for a patient who has sepsis or is suspected of having sepsis and, from the determined amounts of CA 125 conclusions are drawn as to the presence, expected course, the degree and/or the success of measures taken for the therapy of sepsis.

5 Claims, 2 Drawing Sheets

OTHER PUBLICATIONS

Figure 1:
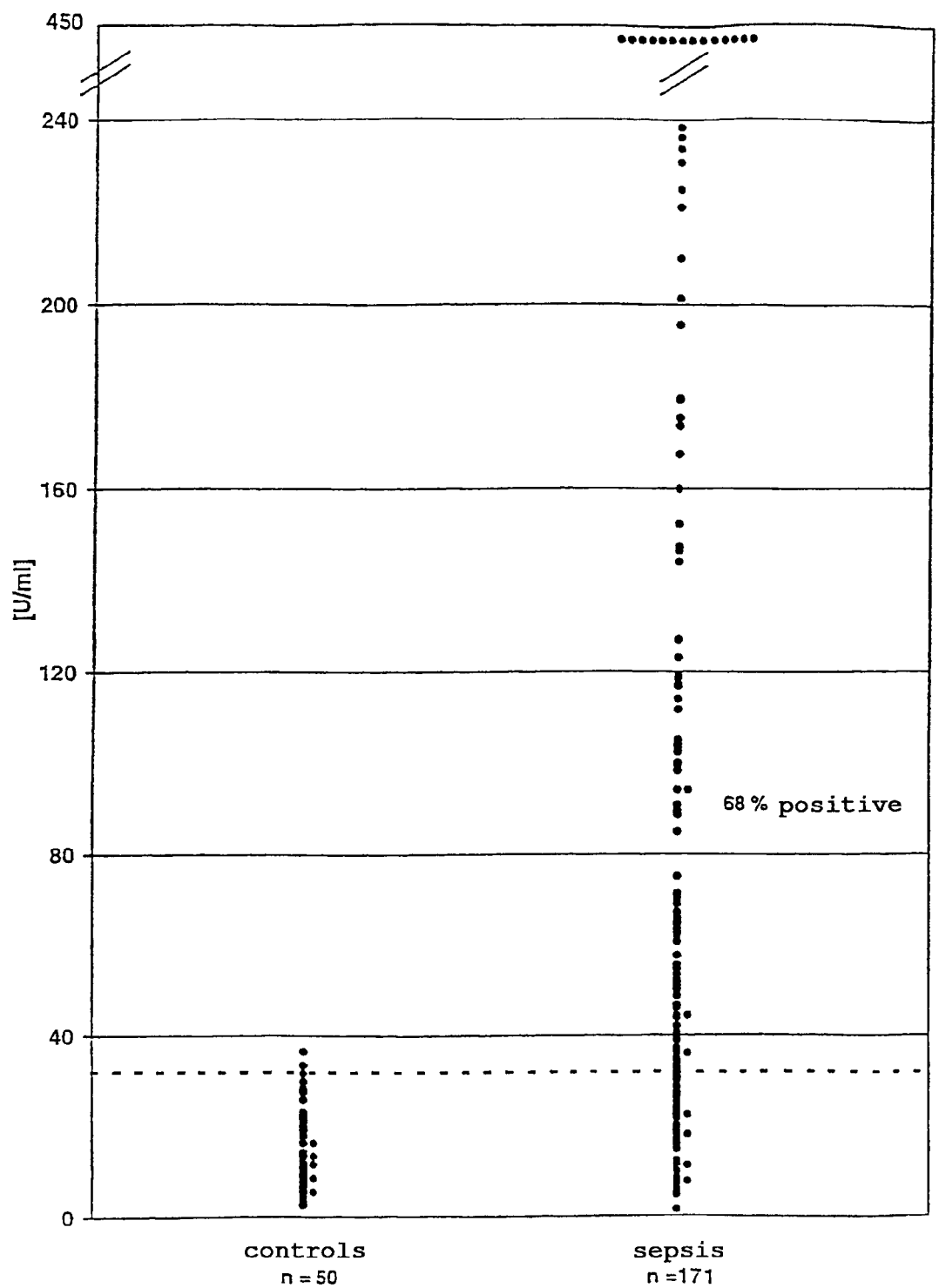

Beishuizen et al., "Endogenous Mediators in Sepsis and Septic Shock," *Advances Clin. Chem.*, 33:55-131, 1999.

Carrigan et al., "Toward Resolving the Challenges of Sepsis Diagnosis," *Clin. Chem.*, 50(8):1301-1314, 2004.

De Quirós et al., "CA125 Serum Levels in Tubercolosis Patients," *Int'l J. Biol. Markers*, 10(3):180-181, 1994.

Gabay and Kushner, "Acute-Phase Proteins and Other Systemic Responses to Inflammation," *New Engl. J. Med.*, 340(6):448-454, 1999.

Health Guide A-Z, *Cancer Antigen 125 (CA-125)*, Internet document, last undated Sep. 26, 2003. pp. 1-3.

Hotchkiss and Karl, "The Pathophysiology and Treatment of Sepsis," *N. Engl. J. Med.*, 348(2):138-150, 2003.

Karzai, et al., "Procalcitonin—A New Indicator of the Systemic Response to Severe Infections," *Infection*, 25:3-8, 1997.

Macri and Vasilev, "Highly Elevated CA 125 and Tubo-Ovarian Abscess Mimicking Ovarian Carcinoma, "*Gynecol Obstet. Invest.*, 37:143-144, 1994.

Marshall et al., "Measures, Markers, and Mediators: Toward a Staging System for Clinical Sepsis. A Report of the Fifth Toronto Sepsis Roundtable, Toronto, Ontario, Canada, Oct. 25-26, 2000," *Crit. Care Med.*, 31(5):1560-1567, 2003 (Abstract only).

Moley et al., "Pelvic Inflammatory Disease," *J. Reprod. Med.*, 41:341-346, 1996.

Moore and Soper, "Clinical Utility of CA 125 Levels in Predicting Laparoscopically Confirmed Salpingitis in Patients with Clinically Diagnosed Pelvic Inflammatory Disease," *Infect. Dis. Obstet. Gynecol.*, 6:182-185, 1998.

Oberholzer et al., "Sepsis Syndromes: Understanding the Role of Innate and Acquired Immunity," *Shock*, 16(2):83-96, 2001 (Abstract only).

Oczenski et al., "Procalcitonin: A New Parameter for the Diagnosis of Bacterial Infection in the Peri-Operative Period," *Eur. J. Anaesthesiol.*, 15:202-209, 1998.

Paavonen et al., "Serum CA 125 in Acute Pelvic Inflammatory Disease," *Brit. J. Obstet. Gynaecol.*, 96:574-579, 1989.

Pannekeet et al., "Dialysate Markers of Peritoneal Tissue During Peritonitis and in Stable CAPD," *Periton. Daily Int'l.*, 15:217-255, 1995.

Petäjä, et al., "Serum Tumor Marker CA 125 Is an Early and Sensitive Indicator of Veno-Occlusive Disease in Children Undergoing Bone Marrow Transplanation," *Clin. Can. Res.*, 6:531-535, 2000.

Redl et al., "Procalcitonin Release Patterns in a Baboon Model of Trauma and Sepsis: Relationship to Cytokines and Neopterin," *Crit. Care Med.*, 28(11):3659-3663, 2000.

Redl and Schlag, "Non-Human Primate Models of Sepsis," *Sepsis*, 2:243-253, 1998.

Zeillemaker et al., "CA 125 Secretion by Peritoneal Mesothelial Cell," *J. Clin. Pathol.*, 47:263-265, 1994.

International Search Report for EPO Application No. 01128848.7, mailed Jul. 18, 2002.

International Search Report for PCT Application No. PCT/EP02/13391, mailed Mar. 5, 2003.

Medline Plus Medical Encyclopeia: Sepsis (http://www.nlm.nih.gov/medlineplus/ency/article/000666.htm, pp. 1-3).

Notice of Allowability in co-pending U.S. Appl. No. 10/511,758.

Office Action dated Sep. 4, 2007 in co-pending U.S. Appl. No. 10/496,096.

Supplemental Notice of Allowability in co-pending U.S. Appl. No. 10/511,756.

Office Action dated Jun. 27, 2007 in co-pending U.S. Appl. No. 10/496,250.

Office Action dated Jan. 7, 2008 in co-pending U.S. Appl. No. 10/497,679.

Office Action dated Jan. 29, 2008 in co-pending U.S. Appl. No. 10/516,618.

\* cited by examiner

METHOD FOR DIAGNOSIS OF SEPSIS WITH DETERMINATION OF CA 125

The present application is a nationalization of PCT Application Serial No. PCT/EP02/13391, filed Nov. 27, 2002, which claims priority to European application No. 01128848.7, filed Dec. 04, 2001.

The invention relates to a novel method for sepsis diagnosis, in which or in the course of which the parameter CA 125 known per se as a typical tumour marker in medical diagnosis is determined.

The invention is based on the detection for the first time of greatly increased concentrations of CA 125 in sera of patients in whom a sepsis had been diagnosed on the basis of clinical findings and simultaneously increased serum concentrations of the known sepsis marker procalcitonin.

The present invention has its origin in intensive research work by the Applicant in relation to further improvements of the diagnosis and therapy of inflammations of infectious aetiology and sepsis.

Inflammations are defined very generally as certain physiological reactions of an organism to different types of external effects, such as, for example injuries, burns, allergens, infections by microorganisms, such as bacteria and fungi and viruses, to foreign tissues which trigger rejection reactions, or to certain inflammatory endogenous conditions of the body, for example in autoimmune diseases and cancer. Inflammations may occur as harmless, localized reactions of the body but are also typical features of numerous serious chronic and acute diseases of individual tissues, organs, organ parts and tissue parts.

In sepsis or septic shock, inflammation-specific reaction cascades spread in an uncontrolled manner over the whole body and may become life-threatening in the context of an excessive immune response. Regarding the current knowledge about the occurrence and the possible role of individual groups of endogenous sepsis-specific substances, reference is made, for example, to A. Beishuizen et al., "Endogenous Mediators in Sepsis and Septic Shock", Advances in Clinical Chemistry, Vol. 33, 1999, 55-131; and C. Gabay et al., "Acute Phase Proteins and Other Systemic Responses to Inflammation", The New England Journal of Medicine, Vol. 340, No. 6, 1999, 448-454. Since the understanding of sepsis and related systemic inflammatory diseases, and hence also the recognized definitions, have changed in recent years, reference is also made to K. Reinhart et al., "Sepsis und septischer Schock" [Sepsis and septic shock], in: Intensivmedizin, Georg Thieme Verlag, Stuttgart, N.Y., 2001, 756-760, where a modern definition of sepsis is given. In the context of the present Application, the term sepsis used is therefore based on the definitions given in the stated literature references.

Whereas at least in Europe the systemic bacterial infection detectable by a positive blood culture long characterized the term sepsis, sepsis is now primarily understood as being systemic inflammation which is caused by infection. Said transformation in the understanding of sepsis has resulted in changes in the diagnostic approaches. Thus, the direct detection of bacterial pathogens was replaced or supplemented by complex monitoring of physiological parameters and, more recently, in particular also by the detection of certain endogenous substances involved in the sepsis process or in the inflammatory process, i.e. specific "biomarkers".

Of the large number of mediators and acute phase proteins which are known or presumed to be involved in an inflammatory process, the ones which are suitable for purposes of clinical sepsis diagnosis are in particular those which occur with high sensitivity and specificity in sepsis or certain phases of a sepsis or whose concentrations change in a dramatic and diagnostically significant manner and which moreover have the stabilities required for routine determinations and reach high concentration values. For diagnostic purposes, the reliable correlation of pathological process with the respective biomarker is of primary importance, without there being any need exactly to know its role in the complex cascade of the endogenous substances involved in the sepsis process.

A known endogenous substance particularly suitable as a sepsis biomarker is procalcitonin. Procalcitonin is a prohormone whose serum concentrations reach very high values under the conditions of a systemic inflammation of infectious aetiology (sepsis), whereas it is virtually undetectable in healthy persons. High values of procalcitonin are also reached in a relatively early stage of a sepsis so that the determination of procalcitonin is also suitable for early diagnosis of a sepsis and for early distinguishing of a sepsis caused by infection from severe inflammations which have other causes. The determination of procalcitonin is furthermore particularly valuable for therapy-accompanying observation of the course of a sepsis. The determination of procalcitonin as a sepsis marker is the subject of the publication by M. Assicot et al., "High serum procalcitonin concentrations in patients with sepsis and infection", The Lancet, Vol. 341, No. 8844, 1993, 515-518; and the patents DE 42 27 454 C2 and EP 0 656 121 B1 and U.S. Pat. No. 5,639,617. Reference is hereby made to said patents and to early literature references mentioned in said publication for supplementing the present description. In recent years, the number of publications on the subject of procalcitonin has greatly increased. Reference is therefore also made to W. Karzai et al., "Procalcitonin—A New Indicator of the Systemic Response to Severe Infection", Infection, Vol. 25, 1997, 329-334; and M. Oczenski et al., "Procalcitonin: a new parameter for the diagnosis of bacterial infection in the peri-operative period", European Journal of Anaesthesiology 1998, 15, 202-209; and furthermore H. Redl et al, "Procalcitonin release patterns in a baboon model of trauma and sepsis: Relationship to cytokines and neopterin", Crit Care Med 2000, Vol. 28, No. 11, 3659-2663; and H. Redl et al., "Non-Human Primate Models of Sepsis", in: Sepsis 1998; 2:243-253; and the further literature references cited therein, as typical of recent published reviews.

The availability of the sepsis marker procalcitonin has given considerable impetus to sepsis research, and intensive efforts are now being made by the Applicant to find further biomarkers which can supplement the procalcitonin determination and/or are capable of providing additional information for purposes of fine diagnosis or differential diagnosis of septic diseases. Thus, a search is being made in particular for further biomarkers for sepsis diagnosis, whose serum or plasma levels are regularly increased but whose determination does not simply duplicate the results of the procalcitonin determination but provides additional information, in particular on the stage of the sepsis process, i.e. information which can rather be assigned to the progress of the sepsis, and/or on the initial or principal organ of a septic process, i.e. localizing information. The aim is in the end the selection of a set of sepsis parameters which are simultaneously determined in the case of sepsis patients or potential sepsis patients, for example using the so-called chip technology or immunochromatographic methods ("point of care" or POC determinations), and in their totality provide an information pattern which clearly surpasses the information value for the determination of only one individual parameter.

The search for potential novel sepsis biomarkers is, however, complicated by the fact that frequently very little or nothing is known about the exact function or about the exact reasons for the occurrence of certain endogenous substances which are involved in the inflammatory or sepsis process.

Since the endogenous substances increased during sepsis are part of the complex reaction cascade of the body, not only are such substances of diagnostic interest but attempts are currently also being made, with considerable effort, to intervene therapeutically in the sepsis process by influencing the formation and/or the concentration of individual substances of this type, in order, for example, to stop as early as possible the systemic spread of the inflammation, which spread is observed during sepsis. In this context, endogenous substances are also to be regarded as potential therapeutic targets.

The results of the experimental testing of a fruitful purely hypothetical approach to the determination of further potential sepsis markers are to be found in DE 198 47 690 A1 and WO 00/22439. There, it is shown that, in the case of sepsis, not only is the concentration of the prohormone procalcitonin significantly increased but also significantly increased concentrations can also be observed for other substances which can be included among the peptide prohormones. The peptide prohormones pro-enkephalin, pro-gastrin releasing peptide (pro-GRP), pro-endothelin-1, pro-brain-natriuretic peptide (pro-BNP), pro-atrial natriuretic peptide (pro-ANP), pro-leptin, pro-neuropeptide-Y, pro-somatostatin, pro-neuropeptide-YY, pro-interleukin-6 or pro-interleukin-10 may be mentioned in this context. While the phenomenon described is well documented, the causes of the increase in the concentrations of prohormones during sepsis are still substantially unexplained.

In the present Application, the result of another hypothetical approach in the search for further biomolecules suitable for sepsis diagnosis is now reported. It is based on the results of measurements of the physiological concentrations of biomarkers, which have been regarded to date as typical tumour markers and have therefore been clinically determined substantially for purposes of tumour diagnosis, in biological samples, in particular serum samples, of sepsis patients for whom no clinical findings at all indicate the presence of tumours.

Surprisingly, it has been found that some biomolecules regarded to date as typical tumour markers are also significantly increased in sepsis. This indicates that these are not formed in a tumour-specific manner but rather indicate a critical physiological process which also affects tissues and organs which release these tumour markers. Although the concentrations of the biomolecules in question are increased during sepsis with high sensitivity, as shown in this Application and simultaneously filed further Applications, there is at the same time no correlation of the measured values with the likewise significantly increased procalcitonin concentrations, i.e. both parameters are found to be increased in individual patients but in some cases to very different extents.

The present invention is based on the evidence, obtained for the first time, that significantly increased physiological concentrations of CA 125 are found in the case of sepsis, which makes these parameters, particularly in combination with the determination of further sepsis parameters, suitable for differential sepsis diagnosis.

The method according to the invention and certain preferred embodiments thereof are defined in more detail in claims 1 to 6.

It was not known to date that the concentrations of CA 125 in biological fluids, in particular the serum concentrations, are significantly increased in the case of sepsis and that the determination of the concentration of CA 125 might therefore also be important for sepsis diagnosis.

On the basis of the present invention, it is possible to use the determination of CA 125 also in the course of a diagnostic sepsis test method. Of particular interest is the suitability of CA 125 as a prognosis marker and marker for monitoring the course of sepsis, in particular as part of a combination measurement with other markers.

In addition to a combination with a procalcitonin determination, a combination of the measurement of CA 125 with the determination of further markers for sepsis and systemic inflammation, which have been regarded to date as typical tumour markers, is particularly suitable, especially with CA 19-9, S100B, or S100A proteins involved in the regulation of inflammations, or with the determination of the novel sepsis markers inflammin (DE 101 19 804.3) and CHP (DE 101 31 922.3) described in the below-mentioned prior unpublished German Patent Applications of the Applicant, and/or with the determination of soluble cytokeratin fragments, in particular of the recently found soluble cytokeratin-1 fragments (sCY1F; DE 101 30 985.6) and of the known tumour markers CYFRA-21 or TPS, and/or of one or more of the abovementioned prohormones. A simultaneous determination of the known inflammation parameter C-reactive protein (CRP) can also be provided. On the basis of the novel results described in this Application and the parallel Applications, a combination with measurements of known biomolecules or biomolecules still to be found, which are suitable as tissue- or organ-specific inflammation markers, should also be considered generally for fine sepsis diagnosis.

The content of said prior Applications of the Applicant is to be regarded as part of the disclosure of the present Application by express reference to these Applications.

CA 125 (cancer antigen 125) is defined as a glycoprotein having a molar mass of about 200 kD and a high carbohydrate content (about 25%), which, as described in Bast et al., 1981, J. Clin. Invest. 68, (1981) pp. 1331-1337, is identified by reaction with a certain specific monoclonal antibody (OC-125). It plays an adjuvant role in the diagnosis, therapeutic monitoring and monitoring of the course of ovarian carcinoma and can also be used as a second marker in the diagnosis of carcinoma of the pancreas (cf. Lothar Thomas (editor): Labor und Diagnose [Laboratory and Diagnosis], Section 34.4, pages 969-973, 5th Edition, 1998 TH-Books Verlagsgesellschaft).

It is known that increased levels of CA 125 can also be measured in a certain number of patients with nonmalignant inflammatory diseases, such as inflammations of the renal pelvis (pyelitis, PID), inflammations of the fallopian tubes (salpingitis), inflammations of the peritoneum (peritonitis) and tuberculosis (cf. for example J. Paavonen et al., (1989), Br J Obstet Gynaecol, 96:574-579; M. M. Pannekeet et al., (1995), Peritoneal Dialysis International, Vol. 15, pp.217-225; C. I. Macri, Gynecol Obstet Invest 1994, 37:143-144; J. Fernandez B. de Quiros et al., The International Journal of Biological Markers, Vol. 10, No. 3, 180-181; J. Petäjä et al., Clin. Canc. Res, Vol. 6, 531-535 (2000); E. Moore et al., Infect. Dis. Obstet. Gynecol. 6:182-185, 1998).

According to our knowledge, no systematic CA 125 measurements have as yet been carried out in the case of patients suffering from sepsis, and nothing was known up to now concerning significantly increased measured values of the typical tumour marker CA 125 in the vast majority of cases in patients with systemic inflammations (sepsis).

A substantial increase in the CA 125 concentrations in the predominant number of sepsis patients was found for the first time in the determinations which are described in the following experimental report with reference to two figures.

IN THE FIGURES

Figure 2:
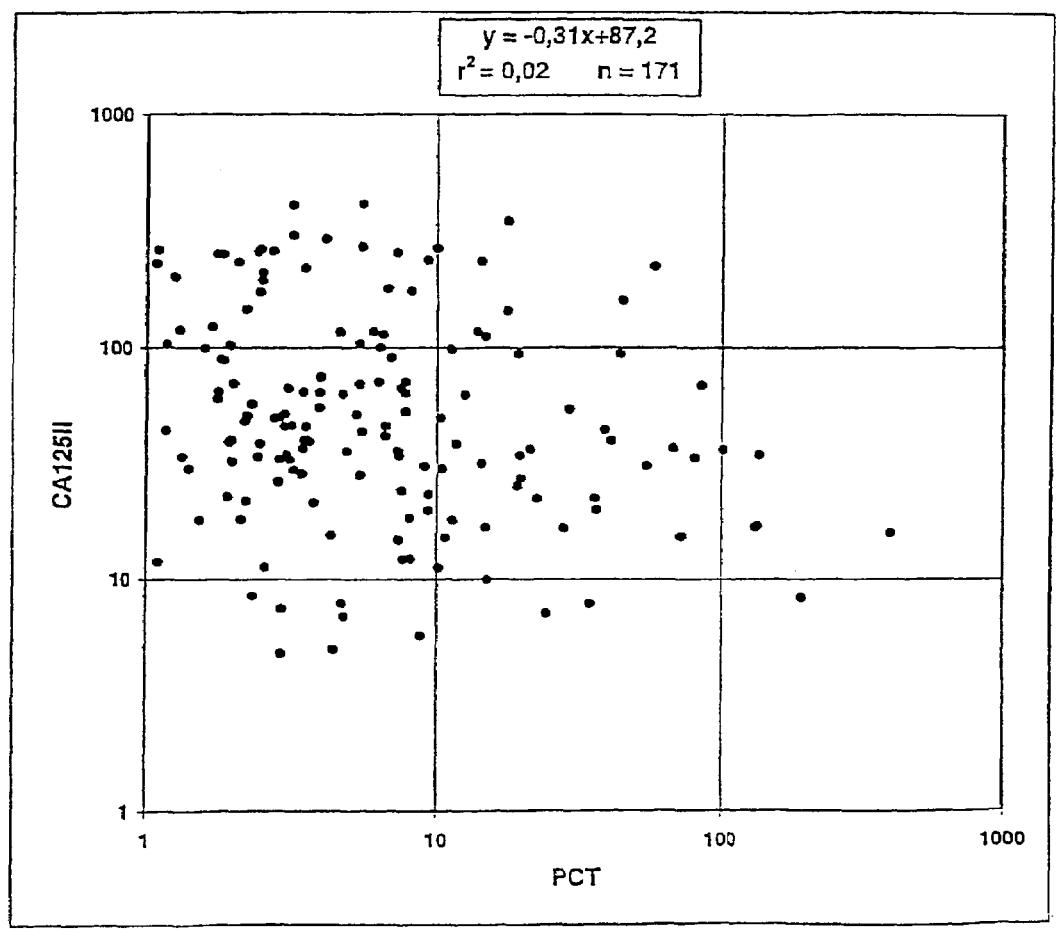

FIG. 1 shows the results of the determination of CA 125 in the sera of 171 sepsis patients in comparison with a group of 50 control persons (blood donors); and FIG. 2 shows the correlation of the results of the CA 125 determinations of 171 sepsis patients of FIG. 1 with the results of the procalcitonin determination.

EXPERIMENTAL REPORT

The serum concentrations of the tumour marker CA 125 were determined in 171 sera of sepsis patients in whom high values of the sepsis marker procalcitonin (PCT) had been found, using a commercial assay for the determination of CA 125 (KRYPTOR-CA125 II from B.R.A.H.M.S Diagnostica GmbH). In 68% of the sera, greatly increased CA 125 concentrations (more than 32 U/ml) were found.

A graph of the measured results is shown in FIG. 1.

If the CA 125 values measured for individual sera are compared with the values measured for PCT, no positive quantitative correlation is found in the sense that the highest CA 125 values are also found in sera in which high PCT concentrations were found. FIG. 2 shows the correlations found in the case of such a comparison. It is evident that high CA 125 values (upper third of the diagram) are also obtained at moderate PCT concentrations, and moderate values for CA 125 at very high PCT concentrations (right third of the diagram).

The fact that the results of the CA 125 determination are substantially independent from those of the PCT determination shows that different effects are measured in spite of the increased values for both parameters in the case of sepsis, which means that the measurement of both parameters provides more information than the measurement of only one of the parameters.

The combination of the determination of CA 125 with that of one or more sepsis markers is therefore suitable for improving the fine diagnosis of sepsis and for improving the prognosis of the course of the disease and for therapy-accompanying monitoring of the course in sepsis patients, it clearly being hoped that the interpretation of the results of such combined determinations based on the exact evaluation of individual cases documented as completely as possible (with, for example, information about the type of infection, reason for and course of the sepsis disease, characteristic data on the age and sex of the patients) will be steadily improved with the number of cases evaluated.

The determination of CA 125 can be carried out by any desired suitable detection method, although the determination in a body fluid of a patient by an immunodiagnostic method using suitable selective antibodies appears to be the most advantageous from practical points of view. Commercial assays for the determination of CA 125 are already available and can also be used in the context of the present invention. Where necessary, good accuracy of measurement in the measuring range relevant for the sepsis diagnosis must be ensured.

Thus, the determination of CA 125 can be carried out for early differential diagnosis and for detection and for the preparation of a prognosis, for assessment of the severity and for therapy-accompanying assessment of the course of sepsis, by determining the content of CA 125 in a sample of a biological fluid of a patient in such a method and drawing conclusions about the presence of a sepsis from the detected presence and/or amount of CA 125 and correlating the result obtained with the severity, the progress of the sepsis and/or the tissue or organ most greatly affected by the sepsis and choosing the possible treatments accordingly and/or estimating the prospects of the treatments.

The invention claimed is:

1. A method of confirming a clinical diagnosis of sepsis in a patient suspected of having sepsis, the method comprising determining the concentration of cancer antigen 125 (CA 125) and procalcitonin in a blood or serum sample derived from said patient; and comparing said concentrations to the corresponding concentrations in a control sample, wherein elevated concentrations of CA 125 and procalcitonin in said patient sample with reference to said control sample is indicative of sepsis.

2. The method according to claim 1, wherein the concentration of CA 125 and procalcitonin is determined by an immunodiagnostic assay.

3. The method according to claim 1, wherein said determining step relating to the concentration of CA 125 and procalcitonin is performed simultaneously.

4. The method according to claim 1, wherein said determining step is performed by means of a chip technology measuring apparatus or an immunochromatographic measuring apparatus.

5. The method according to claim 4, wherein said measuring apparatus provides a measured result that is evaluated with the aid of a computer program.

* * * * *